United States Patent
Holmqvist

(10) Patent No.: US 10,300,204 B2
(45) Date of Patent: May 28, 2019

(54) HOUSING BLANK AND ACTIVATION MEMBER FOR A MEDICAMENT DELIVERY DEVICE, A KIT COMPRISING SUCH BLANKS, AND A MEDICAMENT DELIVERY DEVICE

(71) Applicant: Carebay Europe Ltd, Sliema (MT)

(72) Inventor: Anders Holmqvist, Värmdö (SE)

(73) Assignee: SHL MEDICAL AG, Zug (CH)

( * ) Notice: Subject to any disclaimer, the term of this patent is extended or adjusted under 35 U.S.C. 154(b) by 444 days.

(21) Appl. No.: 15/038,533

(22) PCT Filed: Nov. 20, 2014

(86) PCT No.: PCT/EP2014/075118
§ 371 (c)(1),
(2) Date: May 23, 2016

(87) PCT Pub. No.: WO2015/078760
PCT Pub. Date: Jun. 4, 2015

(65) Prior Publication Data
US 2016/0287798 A1     Oct. 6, 2016

(30) Foreign Application Priority Data

Nov. 26, 2013     (SE) ..................................... 1351406

(51) Int. Cl.
*A61M 5/315*     (2006.01)
*A61M 5/28*     (2006.01)
(Continued)

(52) U.S. Cl.
CPC .......... *A61M 5/31511* (2013.01); *A61M 5/28* (2013.01); *A61M 5/31501* (2013.01);
(Continued)

(58) Field of Classification Search
CPC ................ A61M 5/502; A61M 5/3271; A61M 2005/326; A61M 2005/3247;
(Continued)

(56) References Cited

U.S. PATENT DOCUMENTS 5,925,032 A * 7/1999 Clements ................ A61M 5/34
604/192
2012/0220956 A1     8/2012 Kuracina et al.

FOREIGN PATENT DOCUMENTS

EP     2545957 A1     1/2013
GB     594366 A     11/1947
(Continued)

OTHER PUBLICATIONS

EPO, Int'l Search Report in PCT/EP2014/075118, dated Feb. 10, 2015.

*Primary Examiner* — Imani N Hayman
*Assistant Examiner* — Tiffany Legette
(74) *Attorney, Agent, or Firm* — McDonnell Boehnen Hulbert & Berghoff LLP

(57) ABSTRACT

A housing blank and an activation member blank for a medicament delivery device are disclosed, with a kit including a housing blank and an activation member blank, and a medicament delivery device assembled from the kit. The housing blank includes a mid portion having a through-opening for receiving a proximal end portion of a medicament container assembly, and first and second legs foldable relative to the proximal end portion. The activation member blank includes a central portion and a first and second arm foldable relative to the proximal end portion.

15 Claims, 18 Drawing Sheets

(51) Int. Cl.
| | |
|---|---|
| *A61M 5/32* | (2006.01) |
| *B29B 11/08* | (2006.01) |
| *A61M 5/24* | (2006.01) |
| *A61M 5/50* | (2006.01) |
| *A61M 5/31* | (2006.01) |
| *B29L 31/00* | (2006.01) |

(52) U.S. Cl.
CPC .......... *A61M 5/322* (2013.01); *A61M 5/3271* (2013.01); *B29B 11/08* (2013.01); *A61M 5/24* (2013.01); *A61M 5/3272* (2013.01); *A61M 5/502* (2013.01); *A61M 2005/3142* (2013.01); *A61M 2005/3247* (2013.01); *A61M 2005/3261* (2013.01); *A61M 2207/00* (2013.01); *B29L 2031/7544* (2013.01)

(58) Field of Classification Search
CPC .............. A61M 2207/00; A61M 5/326; A61M 5/3202; A61M 5/3129; A61M 5/31501; Y10T 29/30
See application file for complete search history.

(56) References Cited

FOREIGN PATENT DOCUMENTS

| WO | 2010/034462 A1 | 4/2010 |
|---|---|---|
| WO | 2012/056265 A1 | 5/2012 |

\* cited by examiner ns of US 10,300,204 B2

HOUSING BLANK AND ACTIVATION MEMBER FOR A MEDICAMENT DELIVERY DEVICE, A KIT COMPRISING SUCH BLANKS, AND A MEDICAMENT DELIVERY DEVICE

TECHNICAL FIELD

The present disclosure generally relates to medical devices and in particular to a housing blank and an activation member blank for a disposable medicament delivery device, to a kit comprising the housing blank and the activation member, and to a medicament delivery device assembled from the housing blank and the activation member blank.

BACKGROUND

Disposable medicament delivery devices generally comprise a housing for accommodating a medicament container, and an activation member movably arranged relative to the housing and arranged to expel the drug contained in the medicament container when actuated.

The housing is assembled from several parts, for example two halves which may be snapped together or otherwise assembled. Similarly, the activation member is assembled from several parts. These parts are generally manufactured in a mould, for example by means of injection moulding.

SUMMARY

The more parts that are used for assembling a medicament delivery device, the more expensive the device will be because the production and assembly of each part translates into production time. Moreover, any two parts which are to be assembled to form a housing or an activation member may have small differences meaning that different moulds may be necessary for each part. Moulds are expensive and this investment may reflect on the price of the end product.

The inventor has realised that by minimizing the amount of parts, the production process may be simplified and production time per unit may be reduced. This is reflected in the medicament delivery device price paid by customers/patients.

In view of the above, a general object of the present disclosure is to provide a housing blank which at least mitigates the problems of the prior art.

Another object is to provide an activation member blank which at least mitigates the problems of the prior art.

Hence, according to a first aspect of the present disclosure there is provided a housing blank for a medicament delivery device, wherein the housing blank comprises: a mid portion having a through-opening for receiving a proximal end portion of a medicament container assembly, a first leg defining a first housing side wall and extending from a first end of the mid portion, a second leg defining a second housing side wall and extending from a second end, opposite the first end, of the mid portion, wherein the housing blank has a first fold line which separates the first leg from the mid portion, the first fold line allowing folding of the first leg relative to the mid portion, and wherein the housing blank has a second fold line which separates the second leg from the mid portion, the second fold line allowing folding of the second leg relative to the mid portion.

The housing blank thus provides a single housing part which may be folded to form a housing of a medicament delivery device. The fold lines enable folding of the first leg and the second leg such that a housing may be formed when the first leg and the second leg are folded towards each other thus forming housing side walls. The folded housing blank, which defines a housing of a medicament delivery device, is arranged to accommodate a medicament container.

The housing blank may be moulded in a single mould, instead of two or more as in the prior art, and since the housing blank in a single piece may be folded to form a housing, production steps for assembling several housing parts to form a housing may be discarded.

According to one embodiment the first fold line is adapted to enable folding of the first leg towards the second leg and the second fold line is adapted to enable folding of the second leg towards the first leg.

According to one embodiment the first fold line defines a pivot axis about which the first leg is pivotable in a first direction and the second fold line defines a pivot axis about which the second leg is pivotable in a second direction opposite the first direction.

According to one embodiment the first fold line and the second fold line are parallel.

According to one embodiment the first leg has a first leg end wall portion having a through-opening, and the second leg has a second leg end wall portion having a through-opening, which first leg end wall portion and second leg end wall portion are arranged at differing distances from the mid portion such that the first leg end wall portion and the second leg end wall portion can form a housing end wall when the first leg and the second leg are folded towards each other, wherein the through-openings of the first leg end wall portion and the second leg end wall portion align.

The housing blank is arranged such that when a medicament container is placed in a housing that has been folded from the housing blank, it extends from the mid portion through-opening along the folded first leg and second leg through the aligned through-openings to thereby lock the housing in the folded position. Especially, the extension of the medicament container through the aligned through-openings prevents the first leg and the second leg to be unfolded to their initial positions in which they extend in opposite directions from the mid portion.

According to one embodiment the first leg end wall portion is arranged at a distal end portion of the first leg relative to the mid portion and the second leg wall portion is arranged at a distal end portion of the second leg relative to the mid portion.

According to one embodiment the first leg end wall portion and the second leg end wall portion are perpendicular relative to the first leg and second leg, respectively.

According to one embodiment each of the first leg end wall portion and the second leg end wall portion have cut-outs in their corners.

According to one embodiment each of the first leg and the second leg has guides arranged to interact with respective guide followers of an activation member.

According to a second aspect of the present disclosure there is provided an activation member blank for a medicament delivery device comprising a housing blank according to any of the previous embodiments, wherein the activation member blank comprises: a central portion having a plunger rod, a first arm defining a first activation member side wall and extending from a first end of the central portion, a second arm defining a second activation member side wall and extending from a second end, opposite the first end, of the central portion, wherein the activation member blank has a first fold line which separates the first arm from the mid portion, the first fold line allowing folding of the first arm relative to the mid portion, and wherein the activation member blank has a second fold line which separates the second arm from the mid portion, the second fold line allowing folding of the second leg relative to the distal end portion.

According to one embodiment the first fold line is adapted to enable folding of the first arm towards the second arm and the second fold line is adapted to enable folding of the second arm towards the first arm.

According to one embodiment the first fold line defines a pivot axis about which the first arm is pivotable in a first direction and the second fold line defines a pivot axis about which the second arm is pivotable in a second direction opposite the first direction.

According to one embodiment the first arm has a guide follower for interacting with a guide of a housing, and arranged at a distal end of the first arm relative to the central portion, and wherein the second arm has a guide follower for interacting with a guide of a housing, and arranged at a distal end of the second arm relative to the central portion.

According to one embodiment each of the first arm and the second arm have a respective first edge and a second edge, the first edge of the first arm being aligned with the first edge of the second arm and the second edge of the first arm being aligned with the second edge of the second arm, wherein the guide follower of the first arm is arranged at the first edge of the first arm and the guide follower of the second arm is arranged at the second edge of the second arm.

According to a third aspect there is provided a medicament delivery device kit comprising a housing blank according to the first aspect, and an activation member blank according to the second aspect.

According to a fourth aspect there is provided medicament delivery device for receiving a medicament container, assembled from a housing blank according to the first aspect, and an activation member blank according to the second aspect.

Since the medicament delivery device is assembled from a single piece housing blank, which is locked in its folded position by the medicament container, there is no risk that the housing would fall apart if the medicament delivery device falls to the ground, as could be the case with the prior art where the housing is assembled from several parts.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The words "distal end" and "proximal end" may be used in conjunction with any of the components of the medicament delivery device. In each case, "proximal end" refers to that end of the component which is the end of the component in the direction of medicament administration, and "distal end" refers to the opposite end. It should be noted that the terms "distal" and "proximal" may also be used in conjunction with any portion/component of a housing blank and an activation member blank too; in this case it will be made clear what is intended by these terms, i.e. in relation to what particular portion/component another portion/component is proximal or distal.

FIG. 1 depicts an example of a housing blank 1 for a medicament delivery device. The housing blank 1 is foldable into a housing of a medicament delivery device.

The housing blank 1 comprises a mid portion 3, a first leg 5a and a second leg 5b. The first leg 5a extends from a first end of the mid portion 3. The second leg 5b extends from a second end, opposite the first end, of the mid portion 3. The first leg 5a and the second leg 5b thus extend in opposite directions.

The first leg 5a is separated from the mid portion 3 by means of a first fold line 7a. The second leg 5b is separated from the mid portion 3 by means of a second fold line 7b. The fold line separating the mid portion 3 and the first leg 5a and the fold line separating the mid portion 3 and the second leg 5b are parallel.

The first fold line 7a defines a pivot axis of the first leg 5a, allowing the first leg 5a to be pivoted in a first direction. The second fold line 7b defines a pivot axis of the second leg 5b, allowing the second leg 5b to be pivoted in a second direction opposite the first direction. The first leg 5a and the second leg 5b may thus be folded towards each other.

Figure 1A:
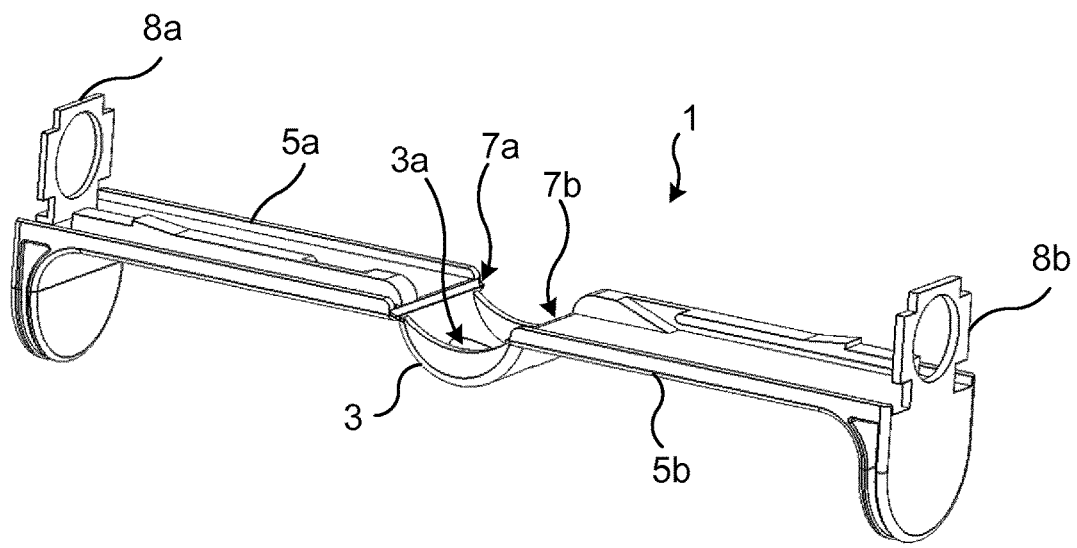
FIGS. 1a-b depict perspective views of a housing blank.
Figure 1B:
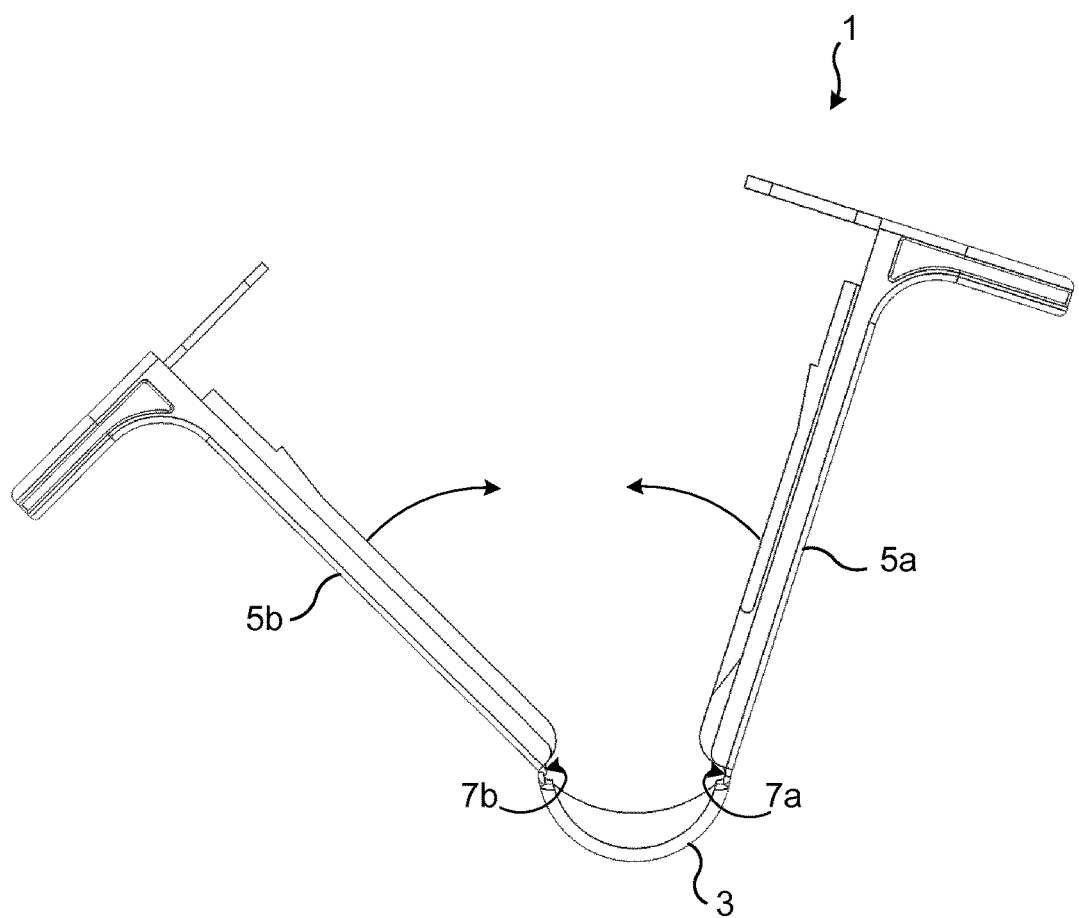
Figure 1C:
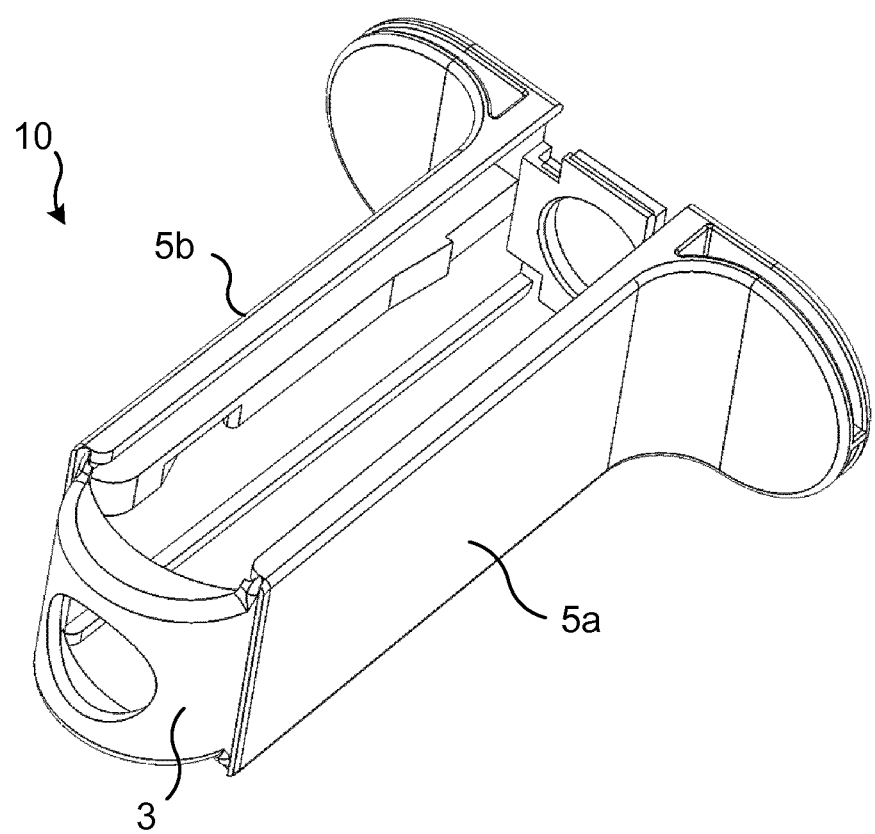
FIG. 1c depicts a perspective view of a housing folded from the housing blank shown in FIGS. 1a-b.

The first leg 5a and the second leg 5b define a first housing side wall and a second housing side wall, respectively, of a housing 10 when the first leg 5a and the second leg 5b have been folded about 90° from their initial position depicted in FIG. 1a to a folded position shown in FIG. 1c. In particular, the arrows in FIG. 1b illustrate how the first leg 5a and the second leg 5b are folded towards each other to the folded position depicted in FIG. 1c.

The mid portion 3 defines a proximal end portion of a housing when the housing blank 1 has been folded to a housing of a medicament delivery device. The mid portion 3 has a through-opening 3a arranged to receive a portion of a medicament container assembly.

The first leg 5a has a first leg end wall portion 8a having a through-opening. The second leg 5b has a second leg end wall portion 8b having a through opening. The through-openings of the first leg end portion 8a and the second leg end portion 8b are dimensioned to be able to receive a medicament container. The width of each of the first leg end wall portion 8a and the second leg end wall portion 8b is less than the width of the first leg 5a and the second leg 5b. There hence exists space between each lateral side of the first leg end wall 8a and the lateral edges of the first leg 5a. Space also exists between each lateral side of the second leg end wall 8b and the lateral edges of the second leg 8b. These spaces allows for an activation member to be received by the housing folded from the housing blank 1.

The first leg end wall portion 8a extends from the first leg 5a and the second leg end wall portion 8b extends from the second leg 5b. According to the example in FIGS. 1a-c the first leg end wall portion 8a is perpendicular relative to the inner surface of the first leg 5a and the second leg end wall portion 8b is perpendicular relative to the inner surface of the second leg 5b. With inner surface is here meant a surface which defines an internal surface of a housing which has been folded from the housing blank 1. It is however envisaged that in variations of the housing blank, the first leg end wall portion could be inclined relative to the inner surface of the first leg, and/or that the second leg end wall portion could be inclined relative to the inner surface of the second leg as long as they are arranged such that the first leg and the second leg can be folded about 90° towards each other.

The first leg end wall portion 8a is arranged at a distal end portion of the first leg 5a, relative to the mid portion 3. The second leg end wall portion 8b is arranged at a distal end portion of the second leg 5b, relative to the mid portion 3.

The first leg end wall portion 8a is arranged at a different distance from the mid portion 3 than the second leg end wall portion 8b. When the first leg 5a and the second leg 5b are folded towards each other, the first leg end wall portion 8a is arranged to abut the second leg 5b and the second leg end wall portion 8b is arranged to abut the first leg 5a. The first leg end wall portion 8a and the second leg end wall portion 8b hence function as distancing members arranged to space the first leg 5a from the second leg 5b.

Figure 2A:
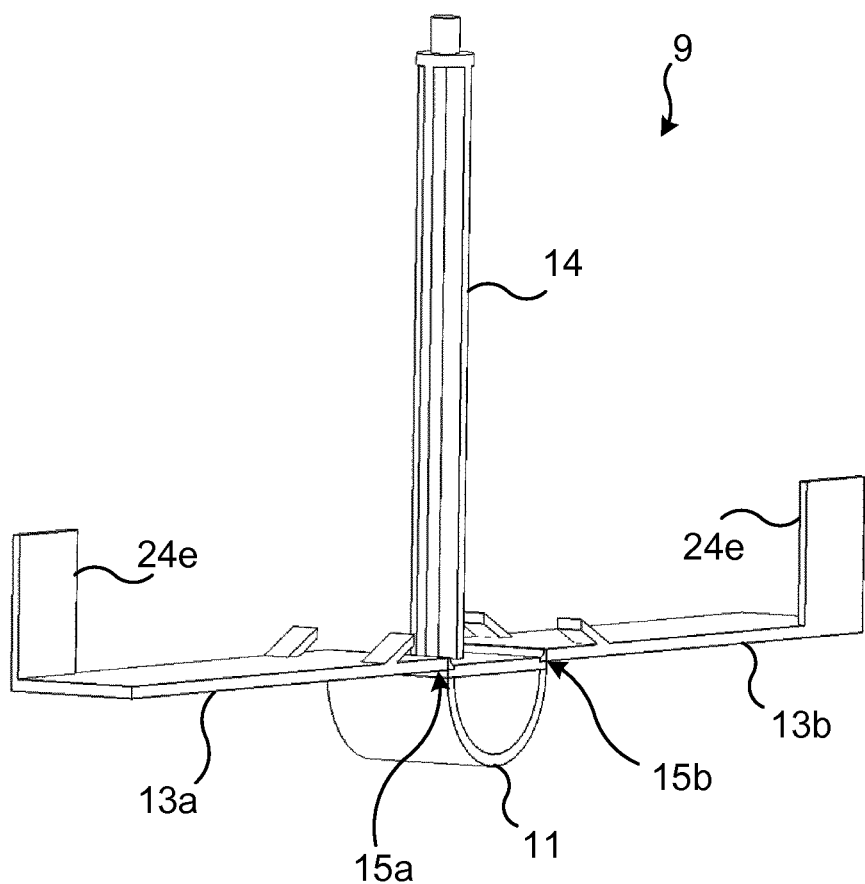
FIGS. 2a-b depict perspective views of an activation member blank.
Figure 2B:
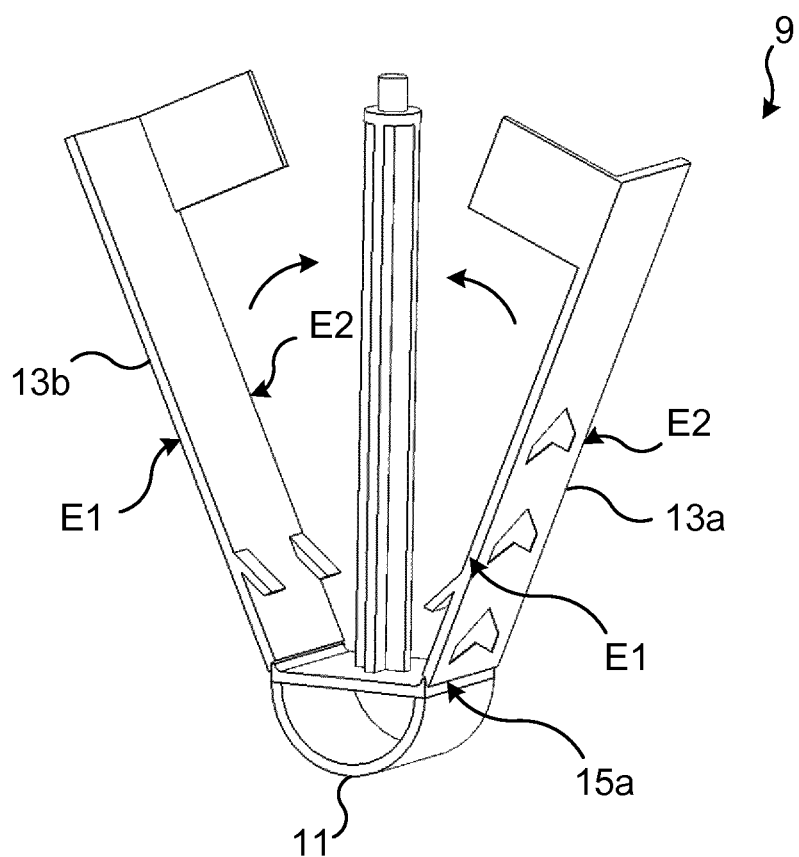
Figure 2C:
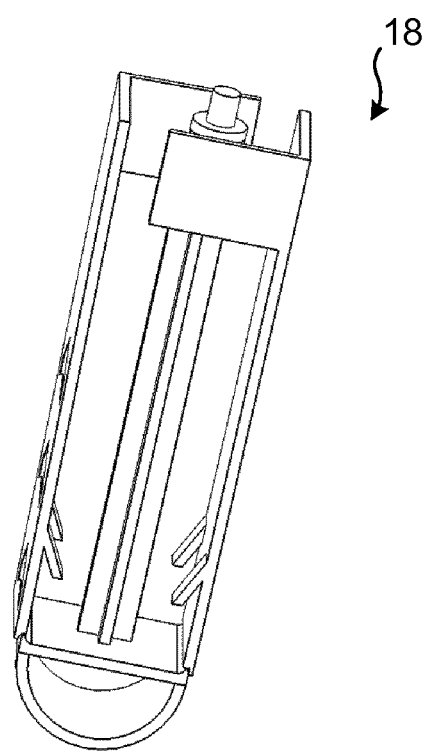
FIG. 2c depict perspective view of an activation member blank folded from the activation member blank shown in FIGS. 2a-b.

The first leg end wall portion 8a and the second leg end wall portions 8b are arranged such that when the first leg 5a is folded about 90° from the initial position towards the second leg 5b and the second leg 5b is folded about 90° from the initial position towards the first leg 5a, the through-opening of the first leg end wall 8a and the through-opening of the second leg end wall 8b align. In this position, the first leg end wall portion 8a and the second leg end wall portion 8b form an end wall of the housing 10. A medicament container assembly may be slid through the aligned through-openings and placed within the housing formed by the folded housing blank 1. Moreover, the first leg end wall 8a and the second leg end wall 8b are arranged at such a distance from the mid portion 3 that a medicament container placed within the housing folded from the housing blank 1 extends through the aligned through-openings. The housing is thereby set in a locked position in the sense that the first leg 5a and the second leg 5b are fixated in the folded position. FIGS. 2a-c illustrate an activation member blank 9 for a medicament delivery device. The activation member blank 9 may be folded to form an activation member of a medicament delivery device.

The activation member blank 9 comprises a central portion 11, a first arm 13a extending from a first end of the distal end portion 11, and a second arm 13b extending from a second end, opposite the first end, of the central portion 11. The first arm 13a and the second arm 13b hence extend in opposite directions. The central portion 11 forms a distal end portion of the activation member folded from the activation member blank 9.

The first arm 13a is separated from the central portion 11 by means of a first fold line 15a. The second arm 13b is separated from the central portion 11 by means of a second fold line 15b. The fold line separating the central portion 11 and the first arm 13a and the fold line separating the central portion 11 and the second arm 13b are parallel.

The first fold line 15a defines a pivot axis of the first arm 13a, allowing the first arm 13a to be pivoted in a first direction. The second fold line 15b defines a pivot axis of the second arm 13b, allowing the second arm 13b to be pivoted in a second direction opposite the first direction. The first arm 13a and the second leg armb may thus be folded towards each other.

The first arm 13a and the second arm 13b define a first activation member side wall and a second activation member side wall, respectively, of an activation member 18 when the first arm 13a and the second arm 13b have been folded about 90° from their initial position depicted in FIG. 2a to a folded position shown in FIG. 2c. In particular, FIG. 2b illustrates by means of the arrows, how the first arm 13a and the second arm 13b are folded towards each other to the folded position depicted in FIG. 2c.

The activation member blank 9 comprises a plunger rod 14 extending from the central portion 11. The plunger rod 14 protrudes perpendicularly from an inner surface of the central portion 11. With inner surface is here meant an internal surface of the activation member folded from the activation member blank 9. The plunger rod 14 hence extends between, and in parallel with, the first arm 13a and the second arm 13b when the activation member blank 9 has been folded to form an activation member. The plunger rod 14 is adapted to interact with a medicament container such that when the activation member blank 9 and the housing blank 1 have been folded and assembled to form a medicament delivery device containing a medicament container, actuation of the activation member relative to the housing results in expulsion of the drug contained in the medicament container.

The first arm 13a has a guide follower 24e, exemplified by a flexible tongue, arranged at a distal end of the first arm 13a relative to the central portion 11. The second arm 13b has a guide follower 24e, exemplified by a flexible tongue, arranged at a distal end of the second arm 13b relative to the central portion 11. Each of the first arm 13a and the second arm 13b has a respective first edge E1 and a second edge E2. The first edge E1 of the first arm 13a is aligned with the first edge E1 of the second arm 13b. The second edge E2 of the first arm 13a is aligned with the second edge E2 of the second arm 13b. The guide follower 24e of the first arm 13a is arranged at the first edge E1 of the first arm 13a and the guide follower 24e of the second arm 13b is arranged at the second edge E2 of the second arm 13b.

The housing blank 1 and the activation member blank 9 together form a medicament delivery device kit from which a medicament delivery device may be assembled.

A method of assembling a medicament delivery device presented herein from a housing blank 1 and an activation member blank 9, or variations of these components, will now be described.

The housing blank 1 and the activation blank 9, and any variations thereof, may for example be created by means of injection moulding. The fold lines 7a, 7b and 15a, 15b may preferably be created as a result of the shape of the mould. Another alternative to create the fold lines 7a, 7b and 15a, 15b is for example by creasing.

The housing blank 1 is folded along its fold lines 7a, 7b to form a housing. The activation member blank 9 is folded along its fold lines 15a, 15b to form an activation member. A medicament container assembly may thereafter be inserted into the housing. The medicament container assembly may be of syringe or cartridge type. A portion of the activation member may then be inserted into the housing such that the guide followers are set to follow their respective first guide, as will be explained in more detail below. Due to the resilient flexibility of the activation member and the guide followers it is possible to insert the activation member into the housing even though the end wall obstructs a direct, longitudinal approach of the guide followers into the first guides.

Thanks to the interlocking structures of the housing and the activation member, and especially due to the blocking and locking function of the end wall, after insertion of the activation member, it becomes impossible to detach the activation member from the housing without using undue force.

Examples of medicament delivery devices assembled from the housing blank 1, and variations thereof, and the activation member blank 9, and variations thereof, will now be described with reference to FIGS. 3-10. In particular, medicament delivery devices which have a mechanism for pulling the needle of the medicament container assembly within the housing 10 protect users from needle sticks post medicament administration will be described. In combination with the lower price of medicament delivery devices which may be provided by means of the foldable properties of the housing and the activation member, more affordable safe disposable medicament delivery devices may be made available to patients in third world countries where blood diseases are more prevalent than in the developed countries.

Figure 3:
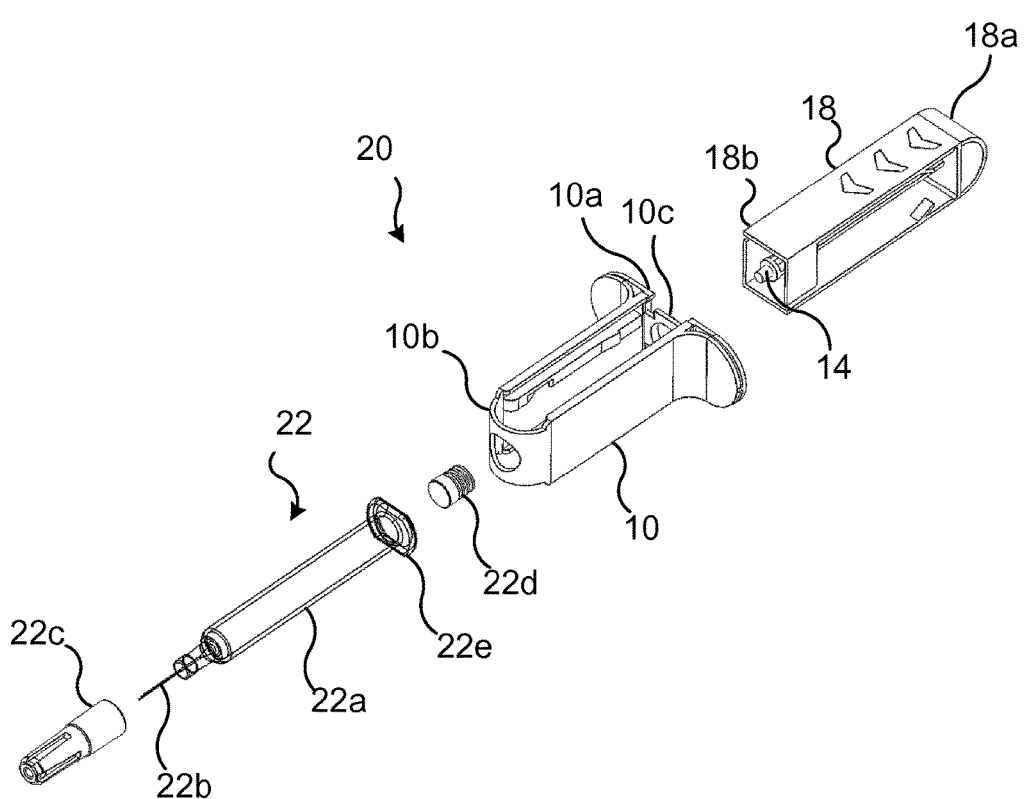
FIG. 3 depicts an exploded view of an example of a medicament delivery device.

FIG. 3 depicts an exploded view of an example of a medicament delivery device 20 and a medicament container assembly 22 of syringe type for use with medicament delivery device 20. The exemplified medicament delivery device 20 comprises a housing 10 and an activation member 18. The exemplified medicament container assembly 22 comprises a medicament container 22a having a flange portion 22e and arranged to hold a liquid medicament, a needle 22b arranged to expel medicament from the medicament container 22a, a needle shield 22c arranged to protect the needle prior to medicament administration and a stopper 22d arranged to seal the medicament container 22a at its distal end and to slide within the medicament container 22a towards the proximal end thereof during medicament administration.

The housing 10 is arranged to receive the activation member 18 from a distal end boa of the housing 10. The housing 10 has an end wall 10c with a central through-opening at the distal end 10a. The housing 10 is arranged to receive the medicament container assembly 22 such that a distal portion of the medicament container assembly 22 is arranged in the through-opening of the end wall 10c.

The activation member 18 has a distal end 18a and a proximal end 18b. The activation member 18 is arranged to move relative to the housing 10 from an extended position in which the activation member 18 protrudes from the housing 10 to a retracted position in which the majority of the activation member 18 is contained within the housing 10. The activation member 18 is arranged to interact with the medicament container assembly 22 when the activation member 18 is moved from the extended position to the retracted position. For this purpose the exemplified activation member 18 has a central plunger rod 14 which interacts with the stopper 22d when the medicament container assembly 22 is arranged in the housing 10.

Figure 4A:
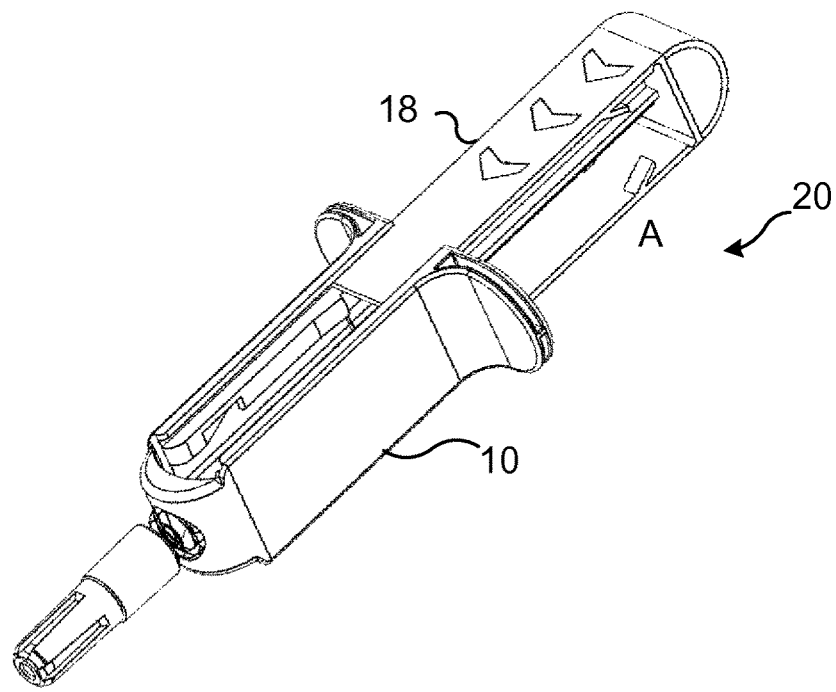
FIGS. 4a-c are perspective view of the medicament delivery device in FIG. 3, showing three steps of the medicament administration process.
Figure 4B:
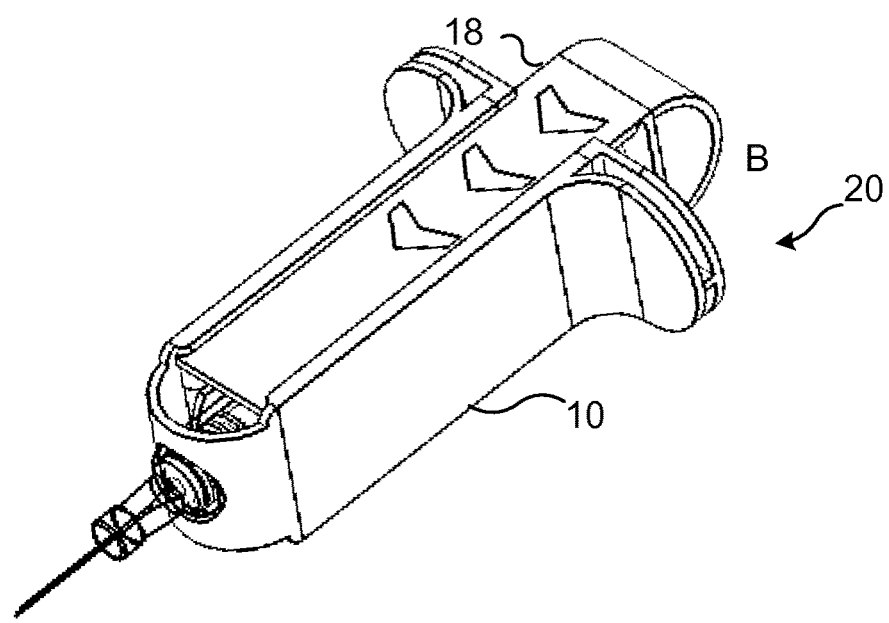
Figure 4C:
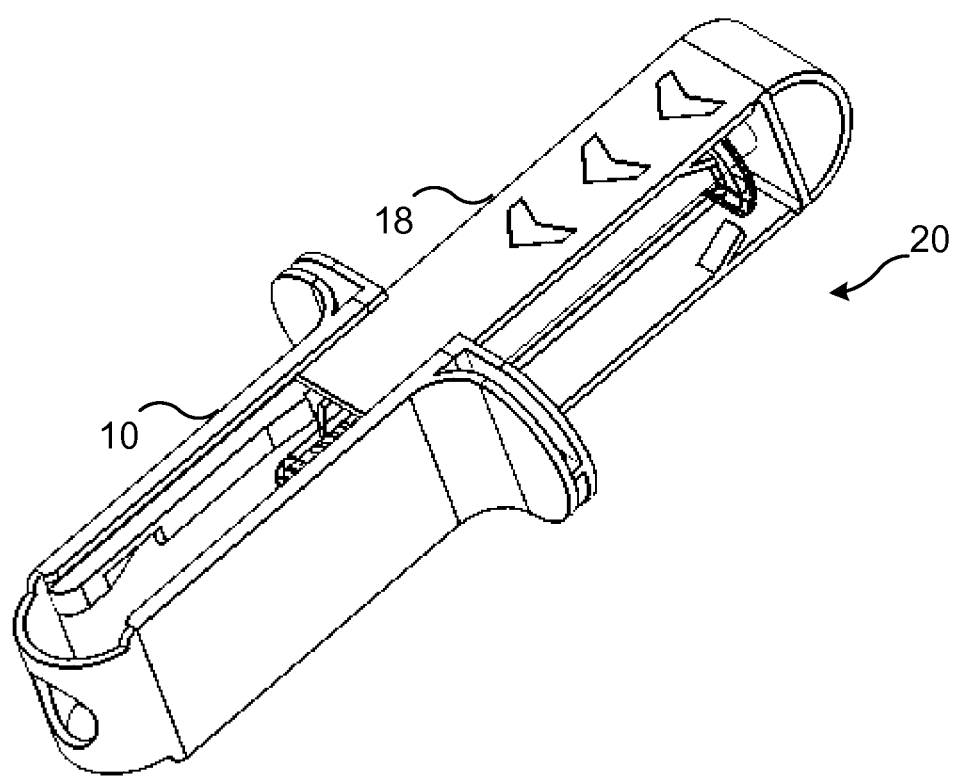

FIG. 4a shows a perspective view of the medicament delivery device 20 in FIG. 3 with the activation member 18 being in the extended position A prior to drug administration. In FIG. 4b the activation member 18 is in the retracted position B in which the content of the medicament container has been expelled from the medicament container 22a. FIG. 4c depicts the medicament delivery device 20 when the activation member 18 again is in the extended position A, post administration, wherein the medicament container assembly, comprising the needle, has been pulled within the housing 10.

Figure 5A:
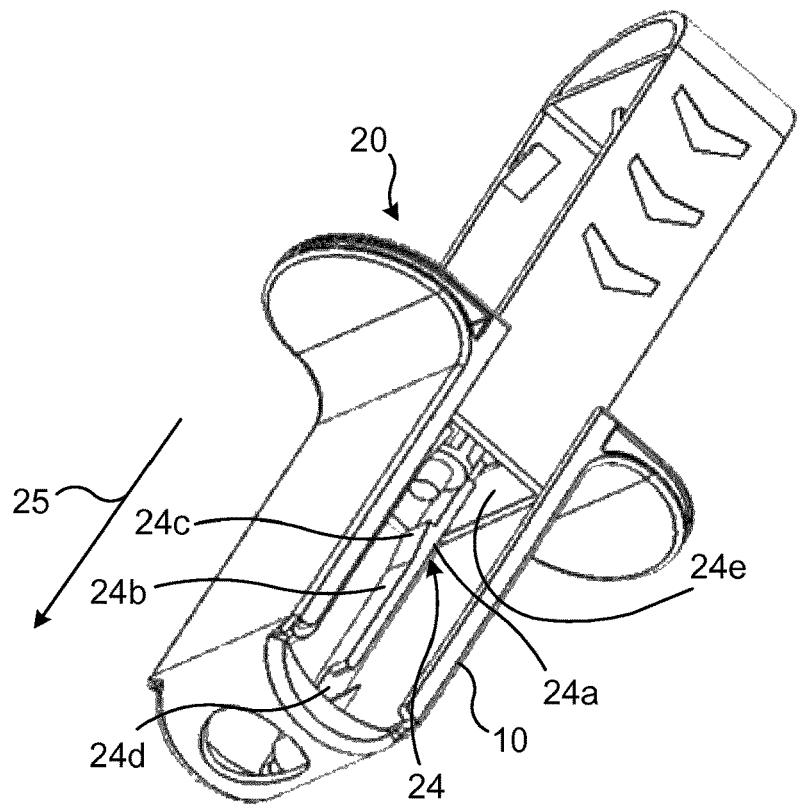
FIG. 5a is a perspective view of the medicament delivery device in FIG. 3.

The functioning of the medicament delivery device 20 will now be described in more detail with reference to FIGS. 5a-6c. FIG. 5a is a perspective view of the medicament delivery device 20. Although states of the medicament delivery device related to the administration of a medicament are shown in FIG. 5a, it should be noted that the medicament container assembly is not included in this figure in order to simplify the presentation.

The housing 10 and the activation member 18 comprise a movement guide mechanism 24 which guides movement of the activation member 18 relative to the housing 10, and which retains the activation member in the extended position A post administration. The movement guide mechanism 24 comprises a first guide 24a, a second guide 24b which has a locking portion 24c, a guide channel 24d between the first guide 24a and the second guide 24b, and a guide follower 24e. The first guide 24a and the second guide 24b extend parallel along a side wall of the housing 10.

According to the present example, the first guide 24a, the second guide 24b and its locking portion 24c, and the guide channel 24d are formed within the housing 10 and the guide follower 24e is formed within the activation member 18. Thus, in the present example, the housing 10 comprises the first guide 24a, the second guide 24b and its locking portion 24c, and the guide channel 24d and the activation member 18 comprises the guide follower 24e. It should however be noted that the converse arrangement is envisaged as an alternative realization. Thus, it is contemplated that the activation member could comprise the first guide, the second guide and its locking portion, and the guide channel and the housing could comprise the guide follower.

According to the present example, the guide follower 24e is flexible and may be bent in a direction away from the inner surface of the housing 10. The guide follower 24e may thus be flexible in a direction towards the centre axis of the housing 10. The exemplified guide follower 24e is defined by a flexible tongue at a proximal end of the activation member 18.

The first guide 24a may be a track in which the guide follower 24e is arranged to slide when the activation member 18 moves from the extended position A prior to being set into its retracted position B. When the activation member 18 is moved axially relative to the housing towards the retracted position B as shown by arrow 25, the guide follower 24e slides along the first guide 24a towards the proximal end of the housing 10. The first guide 24a is connected with the second guide 24b at the proximal end of the first guide 24a via the guide channel 24d. The guide channel 24d extends from the first guide 24a to the second guide 24b and is arranged to enable shifting of the guide follower 24e from the first guide 24a to the second guide 24b. The guide channel 24d is thus arranged to direct the guide follower 24e from the first guide 24a to the second guide 24b. As a proximal end of the guide follower 24e enters the guide channel 24d, it is bent away from the side wall of the housing 10, and as a distal end of the guide follower 24e passes a proximal end of the second guide 24b, the distal end of the guide follower snaps into alignment with the inner surface of the second guide 24b, allowing a return movement of the guide follower 24e along the second guide 24b.

According to the example in FIG. 5a, the guide channel 24d is inclined from the first guide 24a towards the second guide 24b in a direction from the distal end to the proximal end of the housing 10.

According to the example in FIG. 5a, the first guide 24a is closer to the side wall of the housing 10 than the second guide 24b. It is however contemplated that according to a variation of the movement guide mechanism, the second guide could be closer to the side wall of the housing than the first guide.

According to the present example, the second guide 24b is defined by the external surface of one of the side walls of the first guide 24a. The locking portion 24c of the second guide 24b protrudes from this side wall downstream of the guide channel 24d in a direction from the proximal end to the distal end of the housing 10. The locking portion 24c may be wedge-shaped and inclined in a direction from the proximal end to the distal end of the housing 10. Thereby the guide follower 24e is able to pass by the locking portion 24c when the activation member is moved from the retracted position back to the extended position by bending of the guide follower 24e in a direction away from the inner surface of the housing 10.

When the activation member 18 has been set into the extended position again the guide follower 24e will however not be able to move past the locking portion 24c due to the essentially right angle between the locking portion 24c and the side wall defining the second guide 24b, and also due to the longitudinal extent of the guide follower, which imparts a certain bending resistance, in the longitudinal direction, to the guide follower. The guide follower 24e will in this case not bend any further towards the centre axis of the housing 10 from the distal side of the locking portion 24c since there is no force acting on the guide follower in that direction.

The housing 10 and the activation member 18 may comprise two movement guide mechanisms. Thus, for example, the housing may comprise two sets of the first guide, the second guide with locking portion, the guide channel between the first guide and the second guide. The two sets are preferably diagonally disposed on the inner surface of the housing. The activation member may comprise two guide followers arranged to interact with a respective first guide, second guide, and guide channel. By providing additional movement guide mechanisms, a more robust medicament delivery device may be provided in terms of actuation of the activation member 18.

Figure 5B:
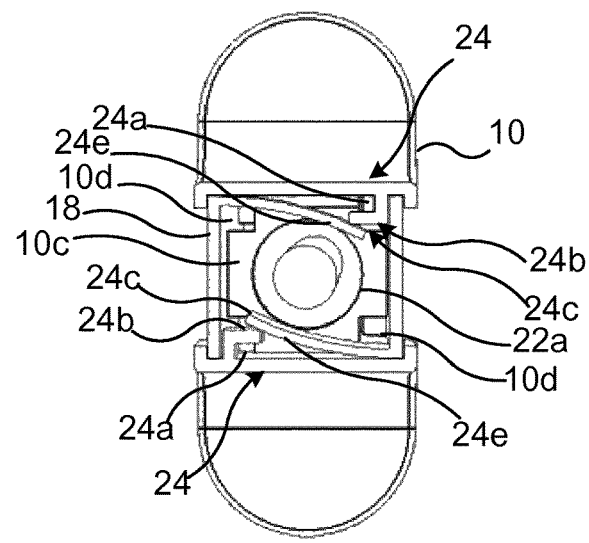
FIG. 5b is a cross section of the medicament delivery device in FIG. 3.

FIG. 5b shows a cross section of the medicament delivery device 20 post medicament administration when the activation member 18 is in a position between the retracted position and the extended position. The guide follower 24e has been shifted from the first guide 24a to the second guide 24b, and abuts the second guide 24b. The guide follower 24e is bent in a direction away from the inner surface of the housing 10, and when further actuated towards the extended position, will be further bent when passing the locking portion 24c. In the example in FIG. 5b, two sets of movement guide mechanisms 24 are depicted.

Figure 6A:
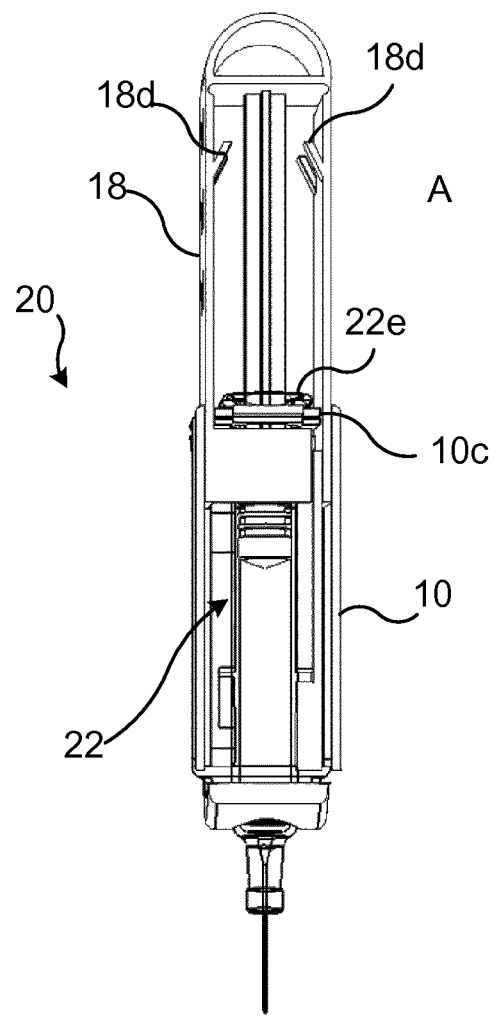
FIGS. 6a-c are longitudinal sections of the medicament delivery device in FIG. 3.
Figure 6B:
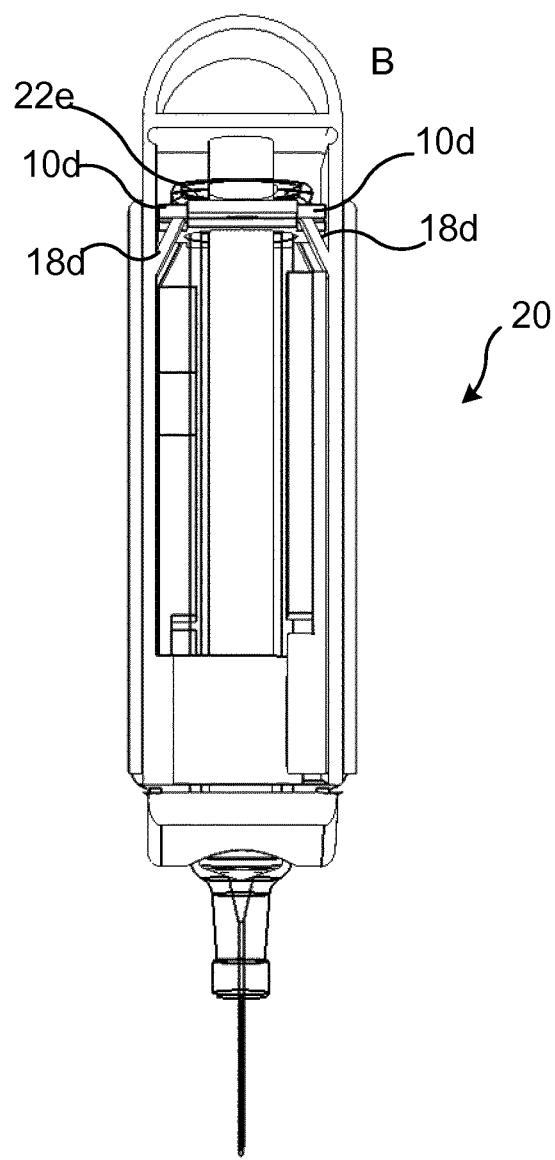
Figure 6C:
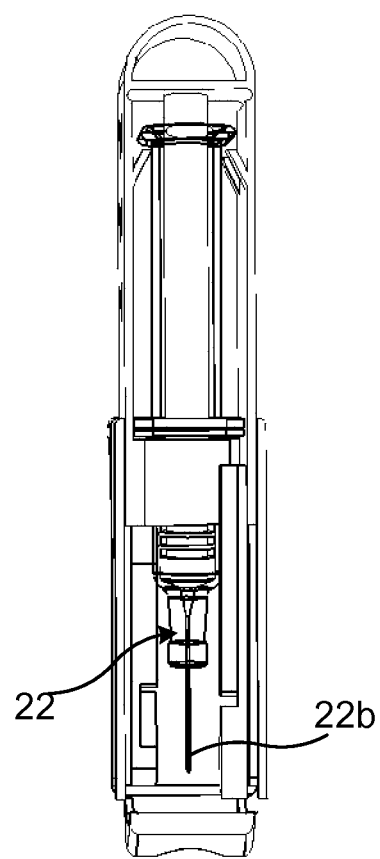

With reference to FIGS. 6a-c the gripping function of the medicament delivery device 20 will now be described in more detail. FIG. 6a depicts a side view of the medicament delivery device 20 when the activation member 18 is in the extended position A prior to medicament administration. The activation member 18 comprises gripping members 18d protruding from the inner surface of the activation member 18 and arranged to engage with the flange portion 22e of the medicament container assembly 22 when the activation member is in the retracted position.

As shown in FIG. 5b, the end wall 10c of the housing 10 has corner cutouts 10d. These corner cutouts 10d are aligned with the gripping members 18d enabling the gripping members 18d to pass through the corner cutouts 10d when the activation member 18 is moved to the retracted position. The corner cutouts 10d are dimensioned such that the flange portion 22e covers a portion of the corner cutouts 10d when the medicament container assembly 22 is arranged in the housing 10. The gripping members 18d protrude from the inner surface of the activation member such that they may interact with the flange portion 22e as the activation member 18 is moved from the extended position to the retracted position.

The exemplified gripping members 18d are flexible and can be bent towards the internal surface of the activation member 18. In particular, the gripping members 18d are arranged such that forces in a direction from the proximal end to the distal end of the activation member 18 applied to the gripping members 18d may resiliently bend the gripping members 18d towards the inner surface of the activation member 18. The gripping members 18d may thereby pass the flange portion 22e and the corner cutouts 10d when the activation member 18 is moved from the extended position to the retracted position. The gripping members 18d thus engage with the flange portion 22e when the activation member 18 is moved back from the retracted position to the extended position. The medicament container assembly 22, including the needle, may thereby be pulled inside the housing 10.

Gripping members 18d may for example be an inclined tab, flange or tongue, with the inclination being defined in a direction from the proximal end to the distal end of the activation member 18.

In FIG. 6b, the medicament delivery device 20 is shown in the retracted position B, wherein the gripping members 18d have moved past the flange portion 22e and moved through the corner cutouts 10d. When the activation member 18 is moved back towards the extended position A, the gripping members 18d engage with the flange portion, since they resist bending when the activation member 18 is moved towards the extended position. As depicted in FIG. 6c, the engagement of the gripping members 18d and the flange portion 22e results in that the medicament container assembly 22 and the needle 22b are drawn inside the housing 10. Needle sticks post medicament administration may thereby be avoided. Moreover, as elaborated hereabove, when the activation member 18 has been set in the extended position A post administration, the locking portion 24c prevents movement of the activation member 18 back to the retracted position B. Furthermore, the guide follower 24e is in this extended position A bent away from the inner wall of the housing 10 and may abut the end wall 10c of the housing 10 such that the activation member 18 is retained within the housing 10. In other words, it is not possible to remove the activation member 18 from the housing 10 after medicament administration, thereby reducing the risk of reuse of the medicament delivery device.

Figure 7A:
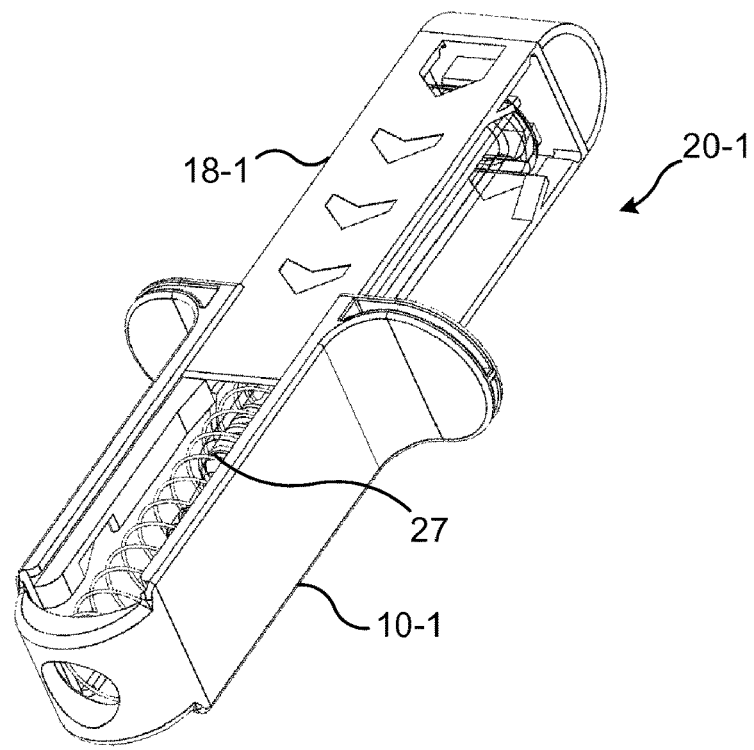
FIGS. 7a-d depict a variation of the medicament delivery device in FIG. 3.
Figure 7B:
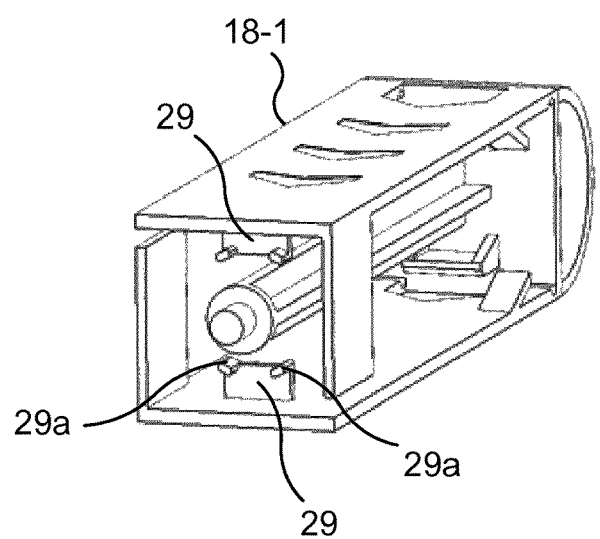

FIG. 7a depicts a variation of the medicament delivery device 20. Medicament delivery device 20-1 comprises an actuation member 27 arranged to bias activation member 18-1 towards the extended position A. The activation member 18-1 comprises supports 29, as shown in FIG. 7b, with which the actuation member 27 is arranged to interact. The actuation member 27 may be an energy accumulating member, for example a spring, such as a helical spring. The actuation member 27 extends between the inner proximate wall of the housing 10-1 and the supports 29. When the activation member 18-1 is in the extended position, the actuation member 27 exerts a smaller force to the supports 29 compared to when the activation member is in the retracted position biasing the activation member 18-1 towards the extended position.

The supports 29 may be protrusions, such as tabs, extending from the internal surface of the activation member 18-1. The supports 29 may further have position holders 29a arranged to restrict lateral movement of the actuation member 27.

Figure 7C:
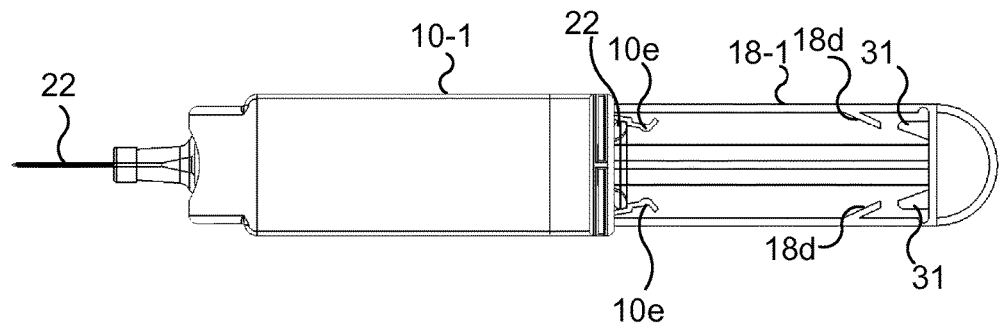
Figure 7D:
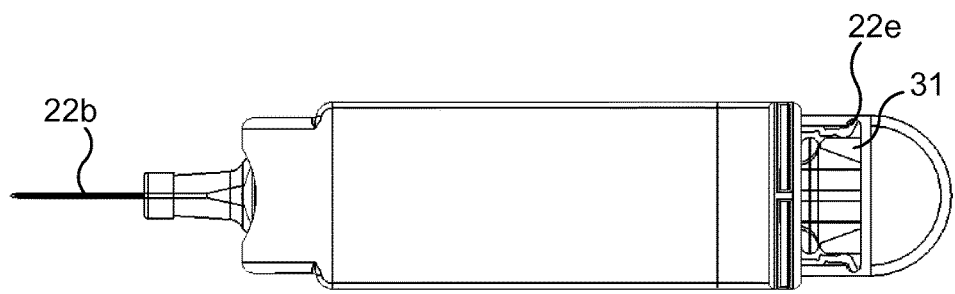

As shown in FIGS. 7c-d, the housing 10-1 has retention members toe arranged to retain the medicament container 22a in position until the activation member 18-1 has obtained its retracted position. The activation member 18-1 has release members 31 arranged to interact with the retention members toe when the activation member 18-1 has obtained its retracted position such that the medicament container may be released. When the gripping members 18d has engaged the flange portion 22e, the medicament container 22a may be moved within the housing such that when the activation member 18-1 is moved towards the extended position.

The retention members according to the present example are a pair of flexible tongues extending from the end wall 10c of the housing 10-1, arranged to interlock with the flange portion 22e such that the medicament container 22a may be maintained in position until the release members 31 bend the retention members toe towards the activation member walls. The release members 31 may be protrusions extending from the distal end wall of the activation member 18-1.

The above-described design with retention members and release members is especially advantageous in the present example which includes actuation member 27 biasing the activation member 18-1 towards the extended position. If the activation member 18-1 is released prior to reaching the retracted position, the central rod of the activation member 18-1 exerts a pulling force to the medicament container due to the activation member being biased, which would pull the medicament container 22a into the housing 10-1 prior to completion of the drug administration, if it was not retained by retention members 10e. The medicament container 22a is thus prevented from movement into the housing 10-1 in case the activation member 18-1 is released prior to reaching the retracted position. When the activation member 18-1 is moved towards the retracted position, interaction between the retention members toe and the release members 31 releases the flange portion 22e and the gripping members 18d engages the flange portion 22e such that movement of the activation member 18-1 towards the extended position pulls the needle 22b into the housing 10-1.

Figure 8:
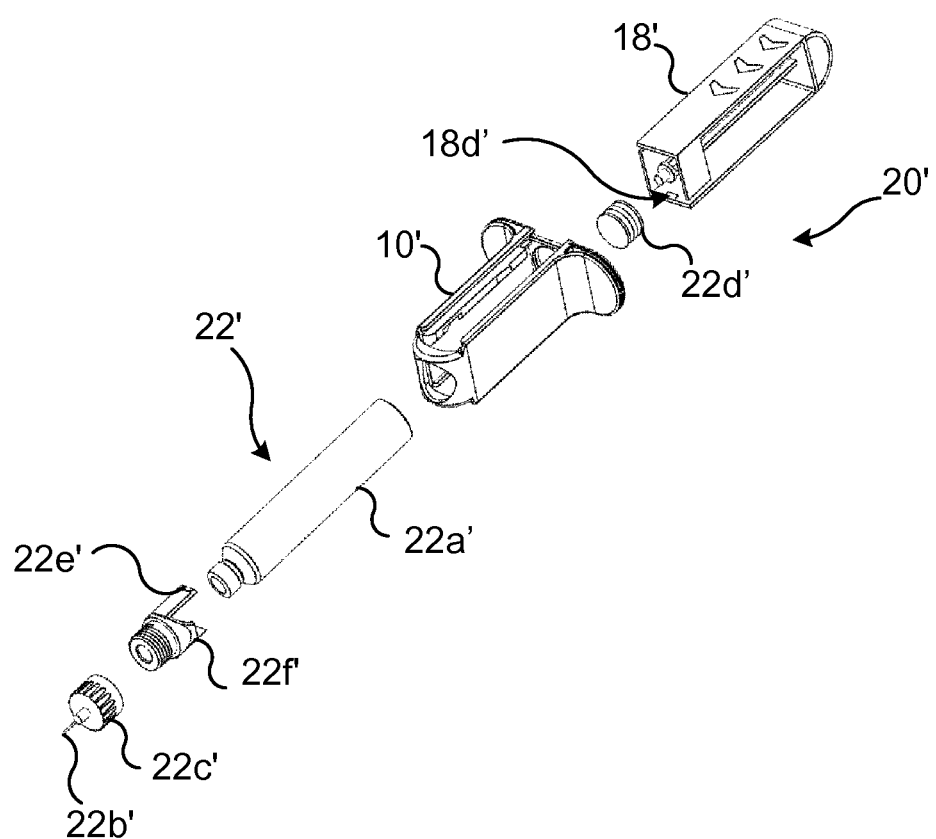
FIG. 8 is an exploded view of an example of a medicament delivery device.

FIG. 8 depicts another example of a medicament delivery device. Medicament delivery device 20' is similar to medicament delivery device 20. Medicament delivery device 20' is however adapted to accommodate a medicament container assembly 22' of cartridge type. The medicament delivery device 20' may comprise a housing 10' similar to the housing 10 described hereabove. In particular, the housing 10' comprises the same movement guide mechanism as medicament delivery device 20. The medicament delivery device 20' also comprises an activation member 18' which has gripping members 18d'.

The medicament container assembly 22' comprises a medicament container 22a', a head member 22f which may be threaded and which has engagement members 22e' arranged to engage with the gripping members 18d', a needle 22b' arranged to be assembled with the head member 22f, and a stopper 22d' with similar function as the stopper previously described. Since the structure of the housing 10' is similar to that already described, including any variation thereof, the housing 10' of medicament delivery device 20' will not be discussed any further herein.

The functioning of medicament delivery device 20' is similar to that of medicament delivery device 20 as shown in FIGS. 4a-c. The activation member 18' can thus obtain an extended position relative to the housing 10' and a retracted position relative to the housing 10'. Moreover, the activation member 18' can be moved back from the retracted position to the extended position, wherein the gripping members 18d' which in the retracted position engages the engagement members 22e' of the head member 22f, pulls the medicament container assembly 22' into the housing 10' when the activation member is moved back to the extended position.

Figure 9:
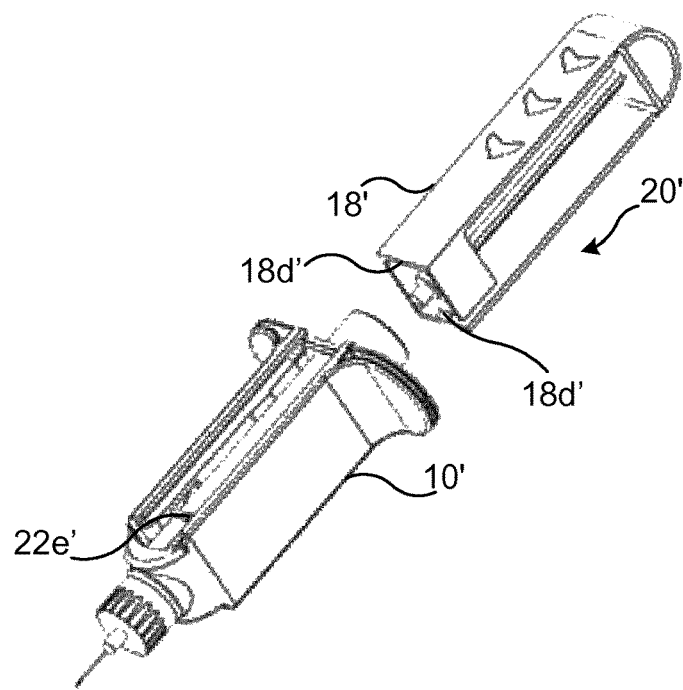
FIG. 9 is a perspective view of the medicament delivery device in FIG. 8.

As can be seen in FIG. 9, the gripping members 18d' may be wedge-shaped and may be arranged at a proximal end of the activation member 18'. The engagement members 22e' of the head member 22f may also be wedge-shaped arranged oppositely compared to the gripping members 18d'. Thus the gripping members 18d' may be inclined in a direction from the proximal end to the distal end of the activation member 18', and the engagement members 22e' may be inclined in the opposite direction. The gripping members 18d' may thereby move across the engagement members 22e' when the activation member is moved into the retracted position, wherein the gripping members 18d' and the engagement members 22e' engage such that movement of the activation member 18' towards the extended position axially displaces the head member 22f and places the entire medicament container assembly 22' within the housing 10' when the activation member 18' is moved back into the extended position.

Figure 10A:
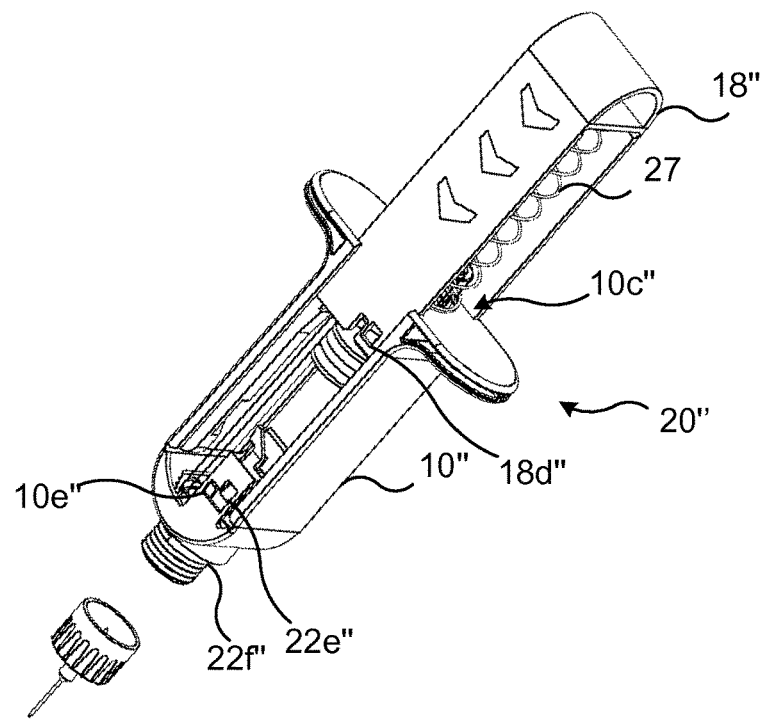
FIGS. 10a-c show a variation of the medicament delivery device in FIG. 8.
Figure 10B:
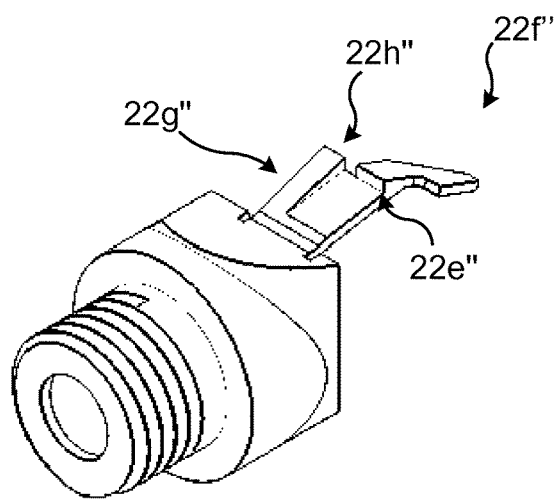
Figure 10C:
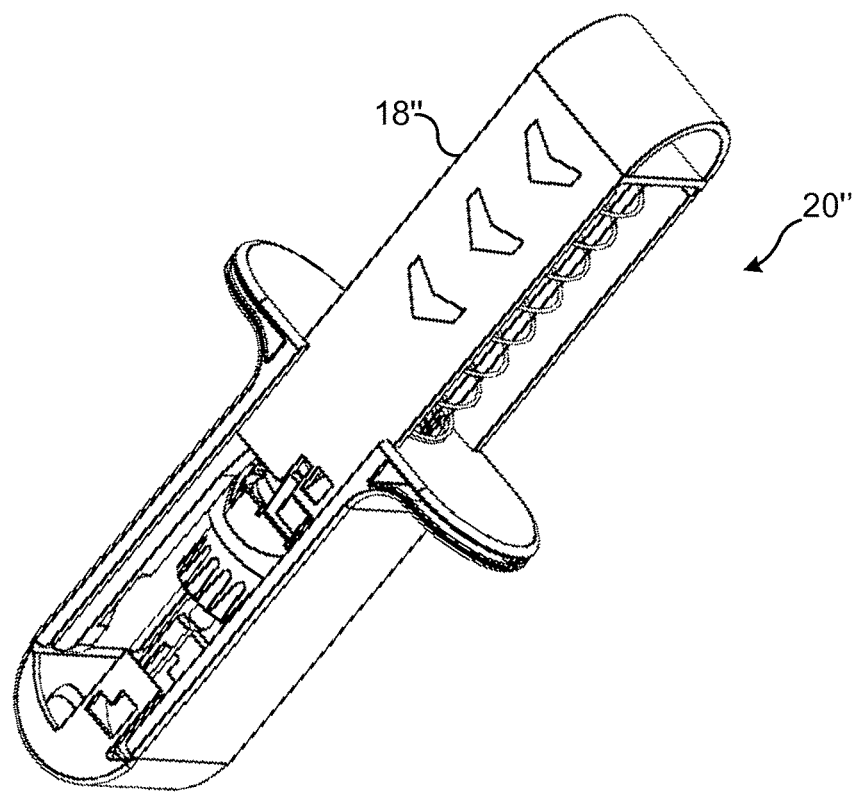

FIGS. 10a-c depict a variation of the medicament delivery device 20'. Medicament delivery device 20" has a housing 10" and activation member 18" which differ from those previously described. It should be noted that the movement guide mechanism of this variation may be implemented according to any variation thereof previously presented.

The medicament delivery device 20" comprises actuation member 27 arranged between the end wall 10c" of housing 10" and a distal inner end wall of the activation member 18". When the activation member 18" is in the extended position, the actuation member 27 exerts a smaller force to the end wall 10c" compared to when the activation member 18" is in the retracted position in which the actuation member 27 biases the activation member 18" towards the extended position.

As shown in FIG. 10*a*, the housing 10" has retention members arranged to retain the head member 22*f* in position until the activation member 18" has obtained its retracted position. The retention member according to the present example is an opening 10*e"* in the proximal end portion of the housing 10". According to the example in FIGS. 10*a-c*, head member 22*f* has engagement member 22*e"* which is a snap, arranged to be snapped into the opening 10*e"*. When snapped into the opening 10*e"* the engagement member 22*e"* prevents the head member 22*f* from falling out from the proximal end opening of the housing 10".

Head member 22*f* also has a snap portion 22*h"* arranged to be snapped into opening 10*e"* of the housing 10", and preventing the head member 22*f* from movement into the housing 10" until the activation member 18" obtains its retracted position. The snap portion 22*h"* hence prevents axial movement, in a direction towards the distal end of the housing 10", of the head member 22*f* prior to the activation member 18" obtains its retracted position. This is especially advantageous in the present example which includes the actuation member 27 biasing the activation member 18" towards the extended position. If the activation member 18" is released prior to reaching the retracted position, the central rod of the activation member 18" exerts a pulling force to the medicament container due to the activation member being biased by the actuation member, which would pull the head member 22*f* into the housing 10" prior to completion of the drug administration, if it was not retained by the snap portion 22*h"*. The head member 22*f* is thus prevented from movement into the housing 10" in case the activation member 18" is released prior to reaching the retracted position. When the activation member 18" is moved towards the retracted position, interaction with the activation member 18" releases the snap portion 22*h"* from the opening 10*e"* and the gripping member 18*d"* releases the engagement member 22*e"* from the housing 10" and interlocks with the engagement member 22*e"* such that movement of the activation member 18" towards the extended position pulls the head member 22*f* into the housing 10".

FIG. 10*b* shows the head member 22*f* which has a flexible tongue 22*g"* on which the engagement member 22*e"* is arranged. The engagement member 22*e"* has a lip arranged to interlock with the gripping member 18*d"* when the activation member 18" is in the retracted position. The gripping member 18*d"* is defined by the proximal wall of a cutout in the proximal end portion of the activation member 18". The gripping member 18*d"* is aligned with the engagement member 22*e"*. The flexible tongue 22*g"* is also provided with the snap portion 22*h"*. When the activation member 18" is moved towards the retracted position, it slides onto the flexible tongue 22*g"*, wherein the flexible tongue 22*g"* is bent inwards such that the snap portion 22*h"* is released from the opening 10*e"* of the housing 10". Furthermore, the gripping member 18*d"* engages the engagement member 22*e"*, which in combination with the released snap portion 22*h"*, allows movement of the head member 22*f* further into the housing 10". FIG. 10*c* illustrates the medicament delivery device 20" when the activation member 18" is back in the extended position and the needle is contained within the housing 10".

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A housing blank for a medicament delivery device, comprising: a mid portion having a through-opening configured to receive a proximal end portion of a medicament container assembly having a distal end portion opposite the proximal end portion; a first leg defining a first housing side wall and extending from a first end of the mid portion; and a second leg defining a second housing side wall and extending from a second end, opposite the first end, of the mid portion; wherein the housing blank has a first fold line that separates the first leg from the mid portion, the first fold line enabling folding of the first leg relative to the mid portion; and the housing blank has a second fold line that separates the second leg from the mid portion, the second fold line enabling folding of the second leg relative to the mid portion, where folding of the first and second legs towards each other forms a housing end wall that will accept the distal end portion of the medicament container such that housing end wall abuts and surrounds the distal end portion to lock the first and second legs relative to each other in a folded position, wherein each of the first and second legs has guides arranged to directly engage with respective guide followers of a movable activation member.

2. The housing blank of claim 1, wherein the first fold line enables folding of the first leg toward the second leg, and the second fold line enables folding of the second leg toward the first leg.

3. The housing blank of claim 1, wherein the first fold line defines a first pivot axis about which the first leg is pivotable in a first direction, and the second fold line defines a second pivot axis about which the second leg is pivotable in a second direction opposite the first direction.

4. The housing blank of claim 1, wherein the first fold line and the second fold line are parallel.

5. An activation member blank for a medicament delivery device having the housing blank as claimed in claim 1, the activation member blank comprising:
a central portion having a plunger rod;
a first arm defining a first activation member side wall and extending from a first end of the central portion; and
a second arm defining a second activation member side wall and extending from a second end, opposite the first end, of the central portion;
wherein the activation member blank has a first fold line that separates the first arm from the central portion, the first fold line enabling folding of the first arm relative to the central portion; and the activation member blank has a second fold line that separates the second arm from the central portion, the second fold line enabling folding of the second arm relative to the central portion,
wherein the activation member can slidably engage with an inside surface of the housing blank as claimed in claim 1.

6. A medicament delivery device for receiving a medicament container, assembled from a housing blank as recited in claim 1 and an activation member blank as recited in claim 5.

7. The housing blank of claim 1, wherein the first leg has a first leg end wall portion having a first through-opening, the second leg has a second leg end wall portion having a second through-opening, and the first and second leg end wall portions are arranged at different respective distances from the mid portion such that the first and second leg end wall portions form the housing end wall when the first and second legs are folded toward each other and the first and second through-openings align.

8. The housing blank of claim 7, wherein the first leg end wall portion is arranged at a distal end portion of the first leg relative to the mid portion, and the second leg wall portion is arranged at a distal end portion of the second leg relative to the mid portion.

9. The housing blank of claim 7, wherein the first and second leg end wall portions are perpendicular relative to the first leg and second leg, respectively.

10. The housing blank of claim 7, wherein the first and second leg end wall portions each have cut-outs in their corners.

11. A medicament delivery device kit, comprising a housing blank as recited in claim 1, and an activation member blank as recited in claim 5.

12. The activation member blank of claim 5, wherein the first fold line enables folding of the first arm toward the second arm, and the second fold line enables folding of the second arm toward the first arm.

13. The activation member blank of claim 5, wherein the first fold line defines a first pivot axis about which the first arm is pivotable in a first direction, and the second fold line defines a second pivot axis about which the second arm is pivotable in a second direction opposite the first direction.

14. The activation member blank of claim 5, wherein the first arm has a first guide follower for interacting with a first guide of housing blank as claimed in claim 1 and arranged at a distal end of the first arm relative to the central portion, and wherein the second arm has a second guide follower for interacting with a second guide of the housing blank as claimed in claim 1 and arranged at a distal end of the second arm relative to the central portion.

15. The activation member blank of claim 14, wherein the first and second arms each have respective first and second edges, the first edge of the first arm being aligned with the first edge of the second arm and the second edge of the first arm being aligned with the second edge of the second arm; the first guide follower is arranged at the first edge of the first arm; and the second guide follower is arranged at the second edge of the second arm.

* * * * *